(12) United States Patent
Plumptre

(10) Patent No.: US 9,731,079 B2
(45) Date of Patent: *Aug. 15, 2017

(54) DRIVE ASSEMBLY SUITABLE FOR USE IN A MEDICATION DELIVERY DEVICE AND MEDICATION DELIVERY DEVICE

(75) Inventor: David Plumptre, Droitwich (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1022 days.

This patent is subject to a terminal disclaimer.

(21) Appl. No.: 13/131,521

(22) PCT Filed: Dec. 1, 2009

(86) PCT No.: PCT/EP2009/066126
§ 371 (c)(1),
(2), (4) Date: Dec. 20, 2011

(87) PCT Pub. No.: WO2010/063704
PCT Pub. Date: Jun. 10, 2010

(65) Prior Publication Data
US 2012/0083745 A1 Apr. 5, 2012

(51) Int. Cl.
*A61M 5/315* (2006.01)
*A61M 5/31* (2006.01)
(Continued)

(52) U.S. Cl.
CPC ...... *A61M 5/31555* (2013.01); *A61M 5/3146* (2013.01); *A61M 5/24* (2013.01);
(Continued)

(58) Field of Classification Search
CPC .......... A61M 5/31545; A61M 5/31548; A61M 5/31551; A61M 5/326; A61M 2005/3206;
(Continued)

(56) References Cited

U.S. PATENT DOCUMENTS 2,816,543 A * 12/1957 Scherer et al. .................. 604/68
3,605,744 A *  9/1971 Dwyer .......................... 604/506
(Continued)

FOREIGN PATENT DOCUMENTS

EP    1704887    9/2006
EP    1923083    5/2008
(Continued)

OTHER PUBLICATIONS

International Search Report for corresponding PCT App. No. PCT/EP2009/066126, mailed Apr. 6, 2010.

*Primary Examiner* — Bhisma Mehta
*Assistant Examiner* — Matthew A Engel
(74) *Attorney, Agent, or Firm* — McDonnell Boehnen Hulbert & Berghoff LLP

(57) ABSTRACT

A drive assembly for a medication delivery device comprising a housing, a drive member moveable in the proximal direction for setting a dose of the medication and in the distal direction for delivering the dose, a piston rod driven by the drive member in the distal direction during movement of the drive member in the distal direction for delivering the dos. A restriction member for restricting proximal movement of the piston rod during proximal movement of the drive member by mechanical interaction of the restriction member with a stop feature of the piston rod. The restriction member and the stop feature are arranged for the piston rod to be moved proximally a first distance during a first proximal movement of the drive member before the restriction member and the stop feature interact mechanically.

14 Claims, 12 Drawing Sheets

(51) Int. Cl.
    *A61M 5/24* (2006.01)
    *A61M 5/50* (2006.01)

(52) U.S. Cl.
    CPC ....... *A61M 5/3156* (2013.01); *A61M 5/31541* (2013.01); *A61M 5/31575* (2013.01); *A61M 5/31585* (2013.01); *A61M 5/50* (2013.01); *A61M 2005/3104* (2013.01); *A61M 2005/3152* (2013.01); *A61M 2005/31518* (2013.01); *A61M 2205/581* (2013.01); *A61M 2205/582* (2013.01); *A61M 2205/583* (2013.01)

(58) Field of Classification Search
    CPC ........ A61M 2005/3217; A61M 5/2033; A61M 5/31578; A61M 5/31576; A61M 5/1458
    See application file for complete search history.

(56) References Cited

U.S. PATENT DOCUMENTS

| | | | |
|---|---|---|---|
| 3,819,091 A * | 6/1974 | Hollender | 222/327 |
| 3,882,863 A * | 5/1975 | Sarnoff et al. | 604/136 |
| 3,934,586 A * | 1/1976 | Easton et al. | 604/208 |
| 4,596,556 A * | 6/1986 | Morrow et al. | 604/70 |
| 4,678,461 A * | 7/1987 | Mesa | 604/157 |
| 4,995,869 A * | 2/1991 | McCarthy | 604/110 |
| 5,300,041 A * | 4/1994 | Haber et al. | 604/207 |
| 5,383,851 A * | 1/1995 | McKinnon et al. | 604/68 |
| 5,503,627 A * | 4/1996 | McKinnon et al. | 604/72 |
| 5,545,147 A * | 8/1996 | Harris | 604/209 |
| 5,569,189 A * | 10/1996 | Parsons | 604/68 |
| 5,679,111 A * | 10/1997 | Hjertman et al. | 604/135 |
| 5,807,334 A * | 9/1998 | Hodosh | A61M 5/20 604/131 |
| 5,865,795 A * | 2/1999 | Schiff et al. | 604/70 |
| 5,891,086 A * | 4/1999 | Weston | 604/70 |
| 6,221,053 B1 * | 4/2001 | Walters et al. | 604/211 |
| 6,419,656 B1 * | 7/2002 | Vetter et al. | 604/90 |
| 6,506,177 B2 * | 1/2003 | Landau | 604/68 |
| 6,972,006 B2 * | 12/2005 | Ferguson | 604/208 |
| 7,156,823 B2 * | 1/2007 | Landau et al. | 604/70 |
| 7,195,616 B2 * | 3/2007 | Diller et al. | 604/224 |
| 7,316,670 B2 * | 1/2008 | Graf et al. | 604/207 |
| 7,678,084 B2 * | 3/2010 | Judson et al. | 604/187 |
| 7,699,802 B2 * | 4/2010 | Steinway et al. | 604/68 |
| 7,857,791 B2 * | 12/2010 | Jacobs | A61M 5/31555 604/224 |
| 8,075,517 B2 * | 12/2011 | Karlsson et al. | 604/82 |
| 8,197,450 B2 * | 6/2012 | Glejbol | A61M 5/31551 604/207 |
| 8,202,256 B2 * | 6/2012 | Moller | A61M 5/24 604/207 |
| RE43,834 E * | 11/2012 | Steenfeldt-Jensen et al. | 604/207 |
| 8,608,709 B2 * | 12/2013 | Moller | A61M 5/24 604/110 |
| 8,672,883 B2 * | 3/2014 | Denning et al. | 604/110 |
| 2005/0165363 A1 * | 7/2005 | Judson et al. | 604/209 |
| 2006/0089593 A1 * | 4/2006 | Landau et al. | 604/68 |
| 2006/0089594 A1 * | 4/2006 | Landau | 604/68 |
| 2006/0270985 A1 * | 11/2006 | Hommann et al. | 604/136 |

FOREIGN PATENT DOCUMENTS

| | | |
|---|---|---|
| EP | 1923085 | 5/2008 |
| WO | 2004/007000 | 1/2004 |
| WO | 2004/035117 | 4/2004 |
| WO | 2008/058666 | 5/2008 |

* cited by examiner

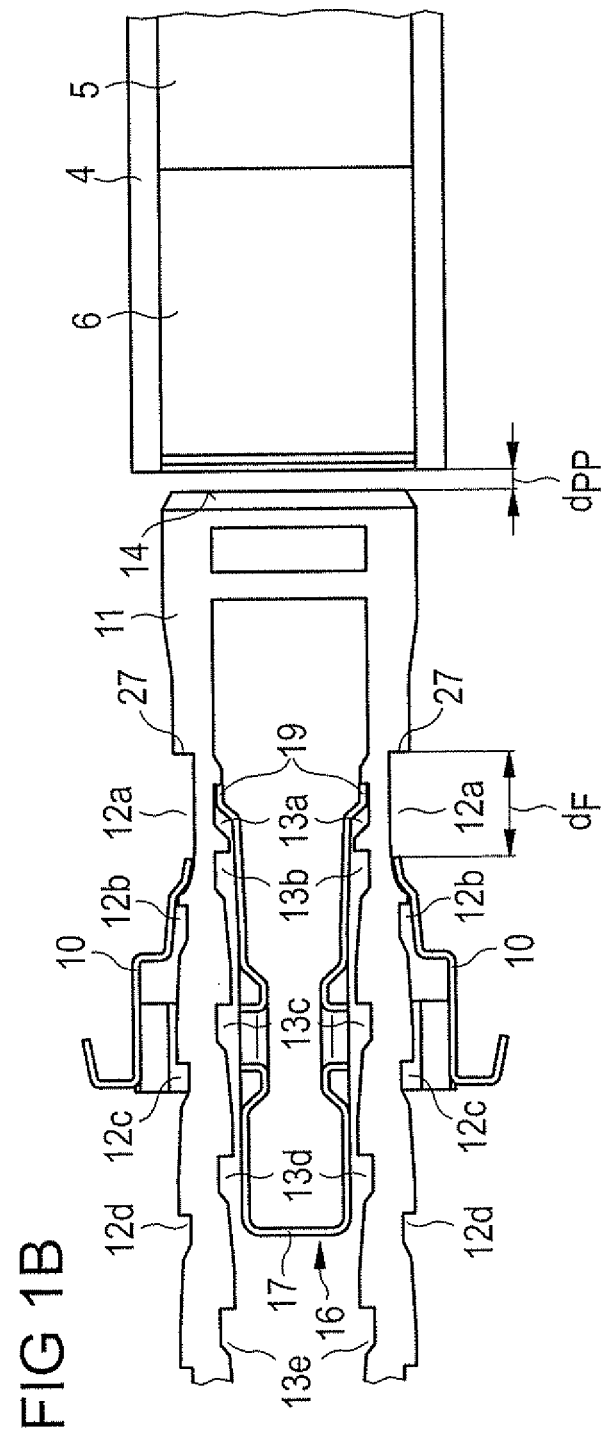

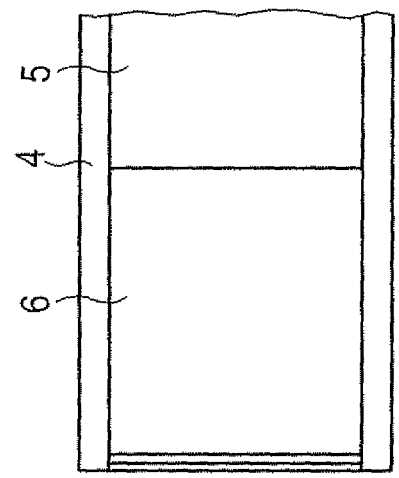
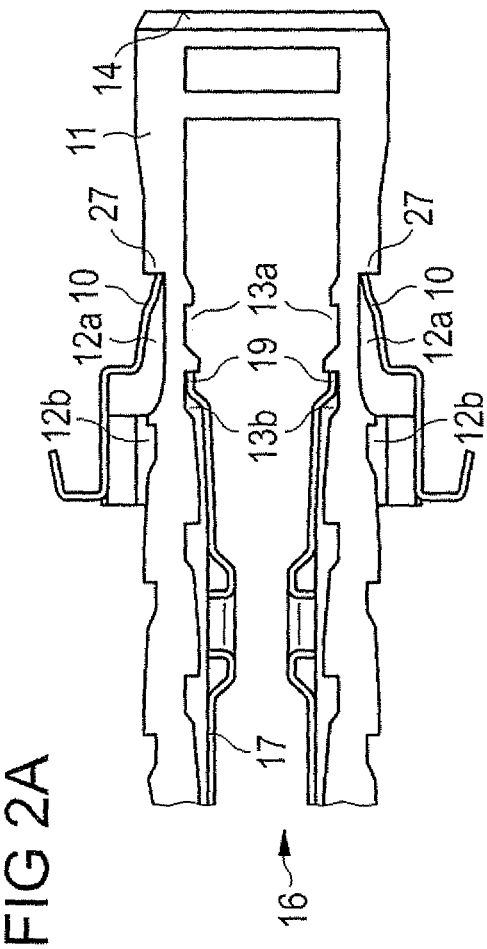
FIG 2A

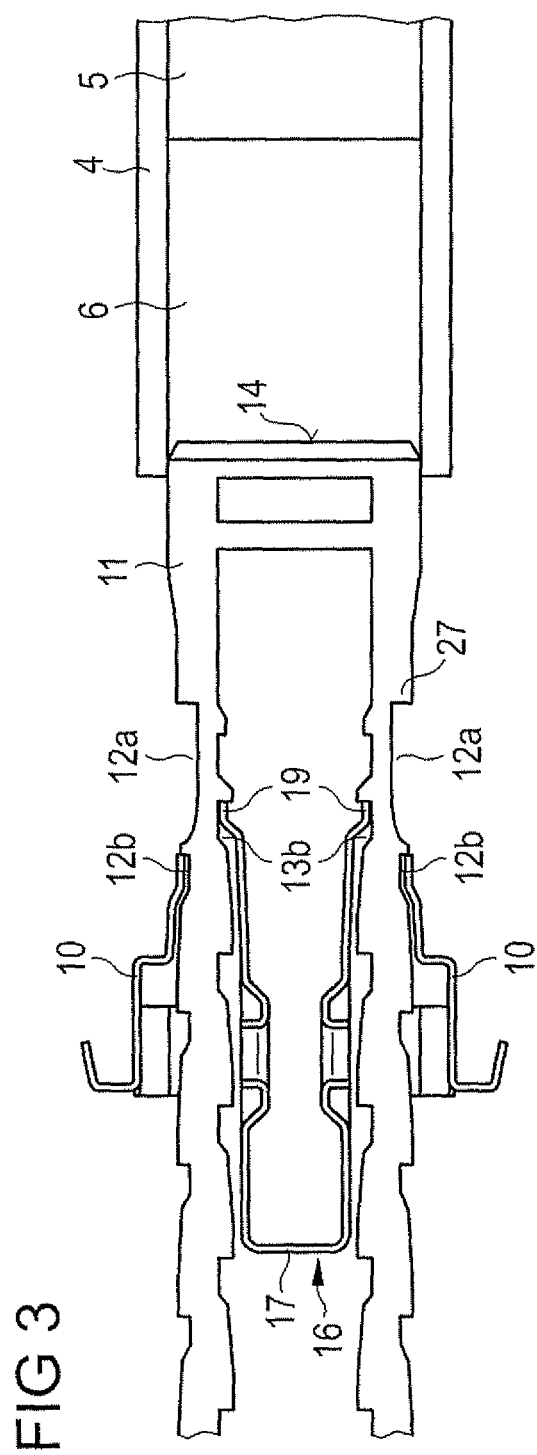

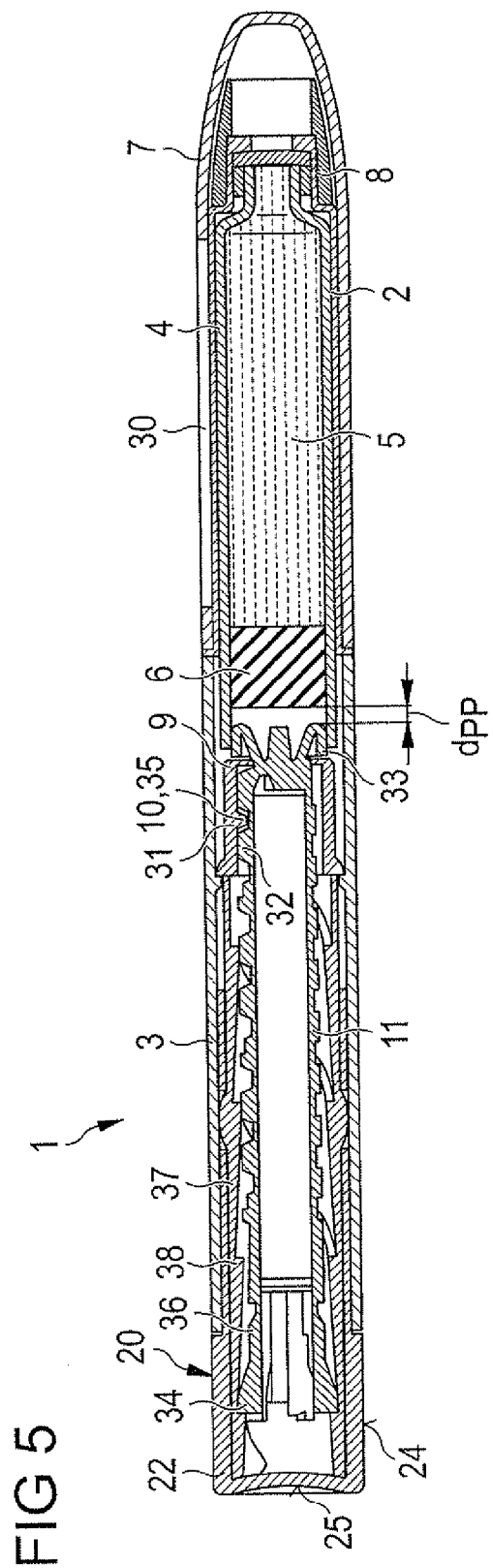

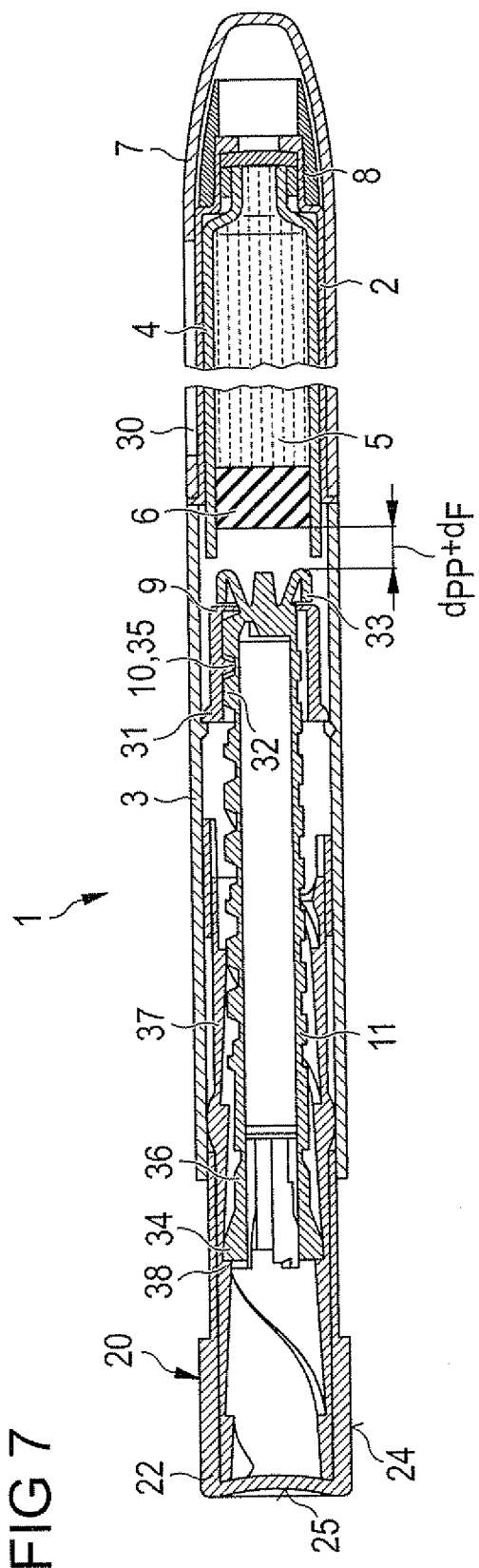

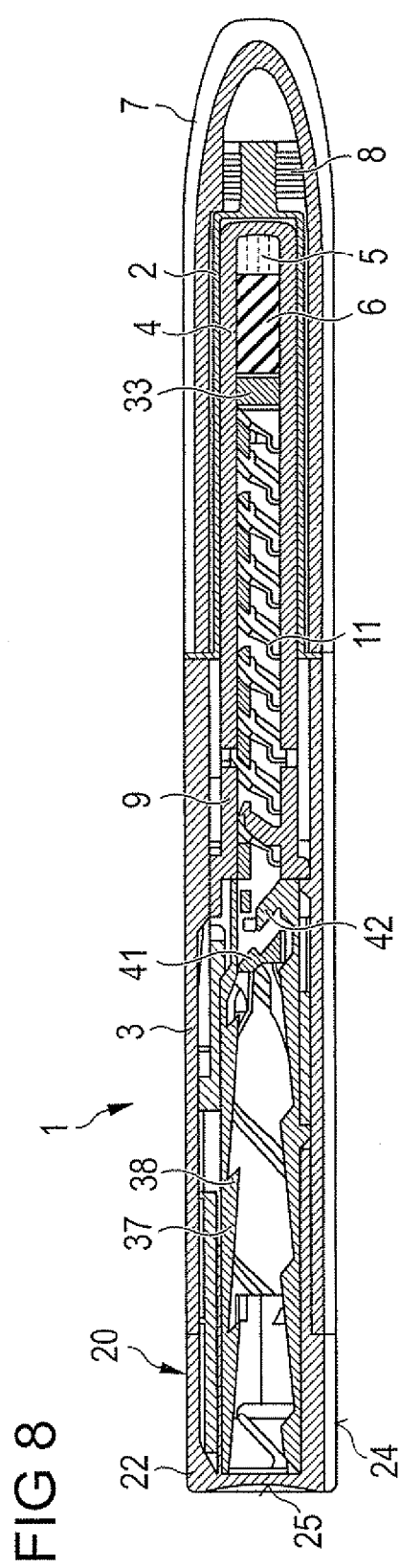

DRIVE ASSEMBLY SUITABLE FOR USE IN A MEDICATION DELIVERY DEVICE AND MEDICATION DELIVERY DEVICE

CROSS REFERENCE TO RELATED APPLICATIONS

The present application is a U.S. National Phase Application pursuant to 35 U.S.C. §371 of International Application No. PCT/EP2009/066126 filed Dec. 1, 2009, which claims the benefit of U.S. patent application Ser. No. 12/326,131, filed on Dec. 2, 2008, which claims priority to European Patent Application No. 08020872.1 filed on Dec. 2, 2008. The entire disclosure content of these applications are herewith incorporated by reference into the present application.

FIELD OF INVENTION

The present invention relates to a drive assembly suitable for use in a medication delivery device, in particular a pen-type device, like a pen-type injector. In particular, the invention may relate to a drive assembly suitable for use in a medication delivery device wherein a number of pre-set doses of a medication may be administered. Furthermore, the present invention may relate to such medication delivery devices where a user may activate the medication delivery device.

BACKGROUND

Such medication delivery devices may have applications if persons without formal medical training, i.e. patients, need to administer an accurate and predefined dose of a medicinal product. In particular, such devices may have application where the medicinal product is administered on a regular or an irregular basis over a short-term or a long-term period.

These circumstances set a number of requirements for medication delivery devices of this kind. The device should be robust in construction, yet easy to use in terms of the manipulation of the parts, understanding by a user of its operation and the delivery of the required dose of medication. Dose setting should be easy and unambiguous. Where the device is to be disposable rather than reusable, the device should be cheap to manufacture and easy to dispose of (preferably being suitable for recycling). To meet these requirements the number of parts required to assemble the device and the number of material types the device is made from should be kept to a minimum.

User operated medication delivery devices are known from U.S. Pat. No. 7,316,670, for example.

Additionally, if the medication is a fluid or a fluid comprises the medication, there are often gaseous inclusions in the fluid, like air bubbles, for example. Such inclusions may be dangerous for the user's health, if they are not removed from the fluid before administration. Also, some elements of a medication delivery device, like a needle, for example, may be filled with gas before the very first dose of medication is dispensed from the device. This may also be dangerous for the user's health, if the gas is not removed. In order to minimize the risk of health damages, gas can be removed from the fluid before the first administration of medication ("priming of the device"). This can be done, for example, by expelling a small dose of the fluid ("the priming dose") from the device while pointing the device in a predetermined orientation, for example needle-up. Thus, gas may be removed from fluid and needle and the risk of injecting a gas into the user is minimized and/or manufacturing tolerances may be removed and/or an initial air gap between the piston rod and the piston of the cartridge may be removed. Of course, the amount of expelled fluid cannot be used for subsequent administration of the medication. As medication is usually rather expensive, the priming dose should be kept at a minimum.

Furthermore, the size of the device, for example its length, should be kept as small as possible, because medication delivery devices, in particular the ones for regular administration of medication, are often carried along by the user and therefore the space required for storing the device matters to the user. In addition, smaller devices are more appealing than larger ones.

SUMMARY

According to one aspect a drive assembly suitable for use in a medication delivery device is provided for, the drive assembly comprising:
  a housing having a proximal end and a distal end,
  a drive member moveable in the proximal direction with respect to the housing for setting a dose of the medication to be delivered and in the distal direction with respect to the housing for delivering the dose,
  a piston rod adapted to be driven by the drive member in the distal direction with respect to the housing during movement of the drive member in the distal direction for delivering the dose, and
  a restriction member for restricting proximal movement of the piston rod with respect to the housing during proximal movement of the drive member by mechanical interaction of the restriction member with a stop feature of the piston rod, wherein
the restriction member and the stop feature are arranged for the piston rod to be moved proximally a first distance during a first proximal movement of the drive member before the restriction member and the stop feature interact mechanically, wherein the first distance which the piston rod moves proximally during the first proximal movement of the drive member (e.g. for setting a priming dose of the medication to be delivered) is larger than a subsequent distance which the piston rod moves proximally during a subsequent proximal movement of the drive member for setting a dose of the medication to be delivered.

The restriction member may be arranged to abut the stop feature for preventing proximal movement of the piston rod that exceeds the first distance during the first proximal movement of the drive member.

According to at least one aspect a medication delivery device comprises the drive assembly and a cartridge, the cartridge comprising a plurality of doses of the medication, in particular at least one priming dose and at least one dose of the medication to be delivered. The device comprises a piston, which is preferably retained in the cartridge. The piston rod is expediently arranged to drive the piston distally with respect to the cartridge for delivering a dose of the medication from the cartridge.

Mechanical interaction of the drive member with the piston rod may tend to move the piston rod proximally during proximal movement of the drive member for setting the dose. This proximal movement with respect to the housing may be stopped when the stop feature and the restriction member interact.

In an initial condition of the drive assembly, the restriction member and the stop feature may be arranged for the piston rod to be moved proximally a first distance during a first proximal movement of the drive member which is actuated starting from the initial condition of the drive assembly or the medication delivery device, respectively. The initial condition may be the condition, in which the drive assembly or the medication delivery device is provided by the manufacturer, e.g. unused but readily assembled, preferably with an unused and full cartridge. In particular, the initial condition may be a state of the drive assembly or the device, in which the piston rod is in an initial position with respect to the housing. That is to say, the piston rod, when it is in the initial position, has not been moved distally with respect to the housing for delivering a dose or for priming the assembly or the device, for example. Accordingly, the drive assembly may be configured to permit movement of the piston rod in the proximal direction during the first actuation of the drive member for setting a dose. Furthermore, the drive assembly may be configured to prevent proximal movement of the piston rod during the second and preferably any subsequent proximal movement of the drive member for setting a subsequent dose. In particular, in the initial condition, before the first actuation, the stop feature and the restriction member may be arranged at a distance from one another, which distance defines the first distance which the piston rod is moved proximally during the first proximal movement of the drive member.

Features described herein above and below in connection with the drive assembly may also refer to the medication delivery device as the device expediently comprises an according drive assembly. Likewise, features described herein above and below in connection with the medication delivery device may also refer to the drive assembly.

In a preferred aspect the piston rod is coupled to the drive member such that the piston rod follows distal movement of the drive member with respect to the housing for dose delivery. The piston rod may follow movement of the drive member with or without ratio of transmission. Thus, the piston rod may be moved by the same distance as the drive member, by a smaller distance than the drive member or by a greater distance than the drive member with respect to the housing. Medication can be dispensed from the cartridge by the piston rod moving the piston distally with respect to the cartridge. The piston rod is expediently coupled to the drive member such that the piston rod is driven in the distal direction with respect to the housing during the first and any subsequent distal movement of the drive member for delivering a dose.

Due to the piston rod following the proximal movement of the drive member during the first proximal movement of the drive member, the piston rod, in particular a surface of the piston rod that is adapted to push the piston in the cartridge in the distal direction with respect to the cartridge during distal movement of the drive member, is moved proximally away from the piston by the first distance before the piston rod is moved distally. Thus, if the piston rod is moved by a given distance during distal movement of the drive member, the distal displacement of the piston with respect to the cartridge can be reduced during the first distal movement of the piston rod, if the piston rod is moved proximally before it is moved distally, such as compared to the piston rod being moved only in the distal direction while the drive member is moved in the proximal and in the distal direction. This is particularly advantageous for the priming of the device as the priming dose expelled from the cartridge may be kept small.

The total distance that the piston travels in the distal direction with respect to the housing during the first distal movement of the drive member is expediently smaller than the total distance the piston rod travels in the distal direction with respect to the housing during the first distal movement of the drive member. Preferably, the first distance the piston rod is moved proximally with respect to the housing during the first proximal movement of the drive member is less than the total distance by which the drive member is moved proximally with respect to the housing during the first proximal movement for setting the dose. The total distance which the piston rod moves in the distal direction with respect to the housing during the first distal movement of the drive member with respect to the housing is greater than the first distance.

In a preferred aspect a priming movement of the drive member, i.e. the movement of the drive member for setting and delivering the priming dose, comprises the first proximal movement of the drive member. The priming dose may be set during the first proximal movement of the drive member. The priming dose may be delivered during the first distal movement of the drive member.

In a preferred aspect the piston rod is arranged at a distance from the piston, in particular before the first proximal movement of the drive member. The piston rod may be separated from the piston by a gap between piston and piston rod, like an air gap, for example. Before a subsequent dose is set and/or delivered, the piston rod may already be mechanically connected to the piston.

The dose which is dispensed from the device during the first distal movement of the drive member corresponds to the distal displacement of the piston with respect to the cartridge. The distal displacement of the piston with respect to the cartridge corresponds to $d_{DM} - d_{PP} - d_F$, wherein $d_{DM}$ is the distance the piston rod travels into the distal direction during the first distal movement of the drive member, $d_{PP}$ is the distance between piston rod and piston before the first proximal movement of the drive member and $d_F$ corresponds to the first distance, by which the piston rod is moved proximally during the first proximal movement of the drive member. Of course, the piston rod may also abut the piston before the first proximal movement. Thus, $d_{PP}$ may be zero or greater than zero.

Accordingly, the distal displacement of the piston within the cartridge may be reduced by the first distance by moving the piston rod by this distance in the proximal direction before the piston rod is moved distally for dose delivery. Thus, the drive assembly may cause a priming dose to be dispensed from the medication delivery which may be smaller than one of or all of the subsequent doses to be dispensed from the device, in particular, if the distal displacement of the piston rod during distal movement of the drive member is fixed for all of the doses which are to be delivered, including the priming dose. Also, the medication delivery device can be reduced in size, in particular in length in the case of a pen-type device, because it is not necessary to arrange the piston rod at a distance from the piston in an initial state of the device that causes only a small priming dose to be expelled from the cartridge by moving the piston rod only in the distal direction during the priming movement of the drive member.

In a preferred aspect the medication delivery device is adapted for dispensing fixed doses of the medication after the device has been primed. For this purpose, the drive assembly may be configured for the piston rod to be moved in the distal direction by a fixed distance during distal movement of the drive member. The piston rod may be moved by this fixed distance during the first, a second, and preferably any subsequent distal movement of the drive member for delivering a dose. However, the dose which is dispensed from the device during the first distal movement of the piston rod (priming dose) is preferably smaller than any subsequent dose on account of the piston rod being moved proximally by the first distance before it is moved distally. Proximal movement of the piston rod is restricted to a small distance during the second and any further subsequent proximal movement of the drive member. The proximal movement of the piston rod might even be completely prevented during the second and any further subsequent proximal movement of the drive member.

According to the present invention, the first distance is in any case larger than a subsequent distance which the piston rod moves proximally during a subsequent proximal movement of the drive member. According to a first embodiment the piston rod does not move proximally at all during the subsequent proximal movement(s) of the drive member for setting a dose of medication to be delivered. A proximal movement of the piston rod during the subsequent movement(s) of the drive member can originate from tolerances of the components within the medication delivery device. Therefore the piston rod can e.g. move a first distance of at least 3 mm in the proximal direction during the first proximal movement of the drive member and at least 0.1 mm during the subsequent proximal movement(s) of the drive member. According to a preferred embodiment the relation of the subsequent distance to the first distance is in the range of 1:50 to 1:5, most preferably in the range of 1:10 to 1:7.

Preferably, the difference between the first distance which the piston rod moves proximally during the first (prime) dose setting compared to the subsequent distance(s) which the piston rod moves proximally during subsequent dose setting is substantially equal to the difference between the distal movement of the piston during subsequent dose delivery compared to the distal movement of the piston during the first (prime) dose delivery.

In a preferred aspect the piston rod comprises a plurality of stop features. The drive assembly is expediently configured for the restriction member to mechanically interact with a different (subsequent) stop feature after distal movement of the drive member for dose delivery. Preferably, the drive assembly is configured for the restriction member to interact with a different stop feature after each distal movement of the piston rod for delivering a dose.

In a preferred aspect the drive assembly is configured for the piston rod to follow proximal movement of the drive member with respect to the housing during the first proximal movement of the drive member and to restrict proximal movement of the piston rod with respect to the housing during the second proximal movement and preferably also during any subsequent proximal movement of the drive member.

In a preferred aspect the piston rod and the restriction member are arranged for a proximal movement of the piston rod to be restricted during a second and preferably any subsequent proximal movement of the drive member for setting a dose. This may be achieved, for example, by the restriction member mechanically interacting with one of the stop features before the second and preferably any subsequent proximal movement of the drive member for setting a dose. A small proximal movement of the piston rod during a second or any other subsequent proximal movement of the drive member for setting a dose can then originate from tolerances of the components within the medication delivery device.

In particular, in a condition other than the initial condition of the drive assembly the restriction member and the associated stop feature—this stop feature is expediently different from the stop feature with which the restriction member interacted during the first proximal movement of the drive member—may be arranged at a distance from one another before dose setting, which is less than the first distance. The restriction member and the associated stop feature may already interact mechanically before the drive member is moved proximally for setting the respective dose, in particular to prevent substantial proximal movement of the piston rod by mechanical interaction of the restriction member and the drive member.

According to one preferred aspect the piston rod is allowed to move proximally for a small distance (which is smaller than the first distance) following the end of each distal medication delivery movement of the piston rod to reduce the pressure of the piston rod on the piston.

In a preferred aspect the respective stop feature is provided on an outer surface of the piston rod. The respective stop feature may be a protrusion (e.g. a tooth) on the outer surface of the piston rod, for example.

In a preferred aspect the stop features are arranged equidistantly along the piston rod. In particular, the projections of the stop features onto a longitudinal axis of the piston rod may be arranged equidistantly. A distance of the projected stop features may correspond to the distance which the piston rod travels in the distal direction with respect to the housing during distal movement of the drive member for dose delivery.

In a preferred aspect the restriction member is secured against at least one of or both of rotational movement with respect to the housing and axial movement with respect to the housing. The restriction member may be provided on the housing, in particular on an inner surface thereof. The restriction member may be fixed to the housing as a separate element or integrated into the housing. Housing and restriction member may be formed unitarily.

In a preferred aspect the piston rod and the drive member are releasably coupled, for example releasably engaged, such that the piston rod may be (completely) decoupled from proximal movement of the drive member with respect to the housing during the second and preferably any subsequent proximal movement of the drive member for setting a dose.

In a preferred aspect the drive member comprises a drive system or a drive sleeve. The drive system may comprise a rack movable with respect to the housing and a rotatable element for engaging the moveable rack, like a gear wheel. The drive sleeve may comprise an internal thread. The piston rod may be threadedly engaged with the internal thread of the drive sleeve.

In a preferred aspect the restriction member engages the piston rod. The restriction member may be a flexible member or a non-flexible member. The restriction member may be a ratchet member, a protrusion, a thread or a part of a thread.

In a preferred aspect the drive assembly is configured for rotational movement of the piston rod with respect to the housing to be restricted or prevented. The drive assembly may be configured for pure axial movement of the piston rod with respect to the housing.

In another preferred aspect the drive assembly is configured for the piston rod to be rotatable with respect to the housing. Thus, the piston rod may rotate while translating in the distal direction with respect to the housing.

Preferably, in this aspect, the piston rod comprises a thread and the restriction member engages the thread of the piston rod. It is expedient for the restriction member to be a thread or a part of a thread in this case. The thread of the piston rod may comprise the respective stop feature. The respective stop feature is preferably a region of the thread that has a different thread angle as compared to an adjacent region of the thread. In particular, the stop feature region of the thread may have a smaller thread angle than adjacent regions. The smaller thread angle may result in a thread region of lower or even zero lead. The respective stop feature may be a shoulder, a step or a dip in the thread of the piston rod, for example.

The term "medication delivery device" may mean a single-dose or multi-dose or pre-set dose, disposable or re-useable device designed to dispense a user selectable or pre-defined dose of a medication, for example 7 pre-defined doses. The medication may comprise insulin, growth hormones, low molecular weight heparins, and/or their analogues and/or derivatives etc. Said device may be of any shape, e.g. compact or pen-type. Furthermore, the device may comprise a needle or may be needle-free. In particular, the term "medication delivery device" may mean a disposable needle-based pen-type device providing multiple pre-defined doses having mechanical and manual dose delivery and dose selection mechanisms, which is designed for use by persons without formal medical training such as patients. Preferably, the medication delivery device is of the injector-type.

The term "housing" may mean any exterior housing ("main housing", "body", "shell") or interior housing ("insert", "inner body"), preferably having an unidirectional axial coupling to prevent proximal movement of specific components. The housing may be designed to enable the safe, correct, and comfortable handling of the medication delivery device or any of its mechanism. Usually, it is designed to house, fix, protect, guide, and/or engage with any of the inner components of the medication delivery device (e.g., cartridge, piston, piston rod) by limiting the exposure to contaminants, such as liquid, dust, dirt etc. In general, the housing may be unitary or a multipart component of tubular or non-tubular shape.

The term "engaged" may particularly mean the interlocking of two or more components of the medication delivery device, e.g. a spline, thread, or meshed teeth connection, preferably the interlocking of meshed teeth of components.

The term "drive member" may mean any component adapted to operate through/within the housing, designed to transfer axial movement through/within the medication delivery device, preferably from an actuation means to the piston rod. In a preferred embodiment the drive member is releasably coupled with the piston rod. The drive member may be of unitary or multipart construction.

The term "drive sleeve" may mean an essentially tubular component of essentially circular cross-section, which may be releasably connected to the piston rod. The said drive sleeve may be of a unitary or multi-part construction. In a more particular embodiment, the drive sleeve may be provided at the proximal end with a user activation means. In a more specific embodiment the user activation means may comprise ribbed surfaces designed to enable the user to grip the drive sleeve securely when setting the device and a smooth concave proximal surface designed to provide a comfortable means of dispensing the device.

The term "releasably engaged" may preferably mean that two components of instant device are engaged for transfer of force or movement in one direction only, preferably during dispense.

The term "piston rod" may mean a component adapted to operate through/within the housing, designed to transfer axial movement through/within the medication delivery device, preferably from the drive member to the piston, for the purpose of discharging/dispensing an injectable product. Said piston rod may be flexible or rigid. It may be a simple rod, a lead-screw, a rack and pinion system, a worm gear system, or the like. The term "piston rod" may further mean a component having a circular or non-circular cross-section. It may be made of any suitable material known by a person skilled in the art and may be of unitary or multipart construction.

In a preferred embodiment the piston rod comprises a series of one or more sets of longitudinally spaced ribs, teeth and/or indentations. In another preferred embodiment the piston rod comprises at least one, more preferably two, external and/or internal helical threads. In another preferred embodiment of the piston rod a first helical thread is located at the distal end and a second helical thread is located at the proximal end of said piston rod, whereby said threads may have the same or, preferably, opposite dispositions. In another preferred embodiment the piston rod comprises threads having the same leads at the proximal and the distal end. Preferably, one of the said threads is designed to engage with a drive sleeve. Alternatively or in addition, the thread which engages with the drive sleeve is formed on a flexible region and/or regions of the said piston rod. Preferably, another of the said threads is designed to engage with a housing, preferably with an inner housing.

The term "gear" may mean a toothed wheel used in conjunction with a rack, preferably a rack to transmit force and/or motion. Preferably, the term "gear" means a gear wheel mounted within a carrier. In an alternative embodiment the term "gear" may mean a lever used in conjunction with a supporting element, e.g. a rib, tooth or an indentation in a housing to transmit force and/or motion. Preferably a first supporting element is located on an inner surface of a housing and a further supporting element is located on a surface of a drive member.

The term "rack" may mean any component having a linear array of ribs and/or indentations and/or teeth. In a preferred embodiment a first rack is located in the housing or the first rack is part of the housing and a second rack is located in the drive member or the second rack is part of the drive member. In a further preferred embodiment one and/or both, more preferably one, of the racks located on the housing or on the drive member is flexible and/or pivotable and/or movable in one or more axial directions, more preferably in one axial direction.

The "distal end" of the device or a component of the device may mean the end, which is closest to the dispensing end of the device.

The "proximal end" of the device or a component of the device may mean the end, which is furthest away from the dispensing end of the device.

The term "mechanically interacting" may mean any mechanical interaction that is suitable for preventing further proximal movement of the piston rod with respect to the housing during proximal movement of the drive member, for example by the restriction member having moved into abutment with a stop feature. The piston rod may be moved proximally during the first proximal movement of the drive member until the restriction member abuts the stop feature and additional proximal movement of the piston rod with respect to the housing is prevented by the restriction member abutting the stop feature. The drive member may be moved further on in the proximal direction with respect to piston rod and housing, after the restriction member and the stop feature have moved into abutment.

Further features, advantages and expediencies become apparent from the following description of the exemplary embodiments in connection with the figures.

BRIEF DESCRIPTION OF THE FIGURES

FIG. 1B shows an enlarged simplified view of a part of the first embodiment of the medication delivery device in the first, cartridge full, position;

FIG. 2A shows an enlarged simplified view of a part of the first embodiment of the medication delivery device in the second, priming dose set, position;

FIG. 3 shows an enlarged simplified view of a part of the first embodiment of the medication delivery device in a third, priming dose delivered, position;

FIG. 5 shows a sectional view of a second embodiment of a medication delivery device in a first, cartridge full, position;

FIG. 7 shows a sectional view of the second embodiment of the medication delivery device in a second, priming dose set, position;

FIG. 8 shows a sectional view of the second embodiment of the medication delivery device in a forth, final dose delivered, position;

Like elements, elements of the same kind and identically acting elements are provided with the same reference numerals throughout the figures.

DETAILED DESCRIPTION

Figure 1:
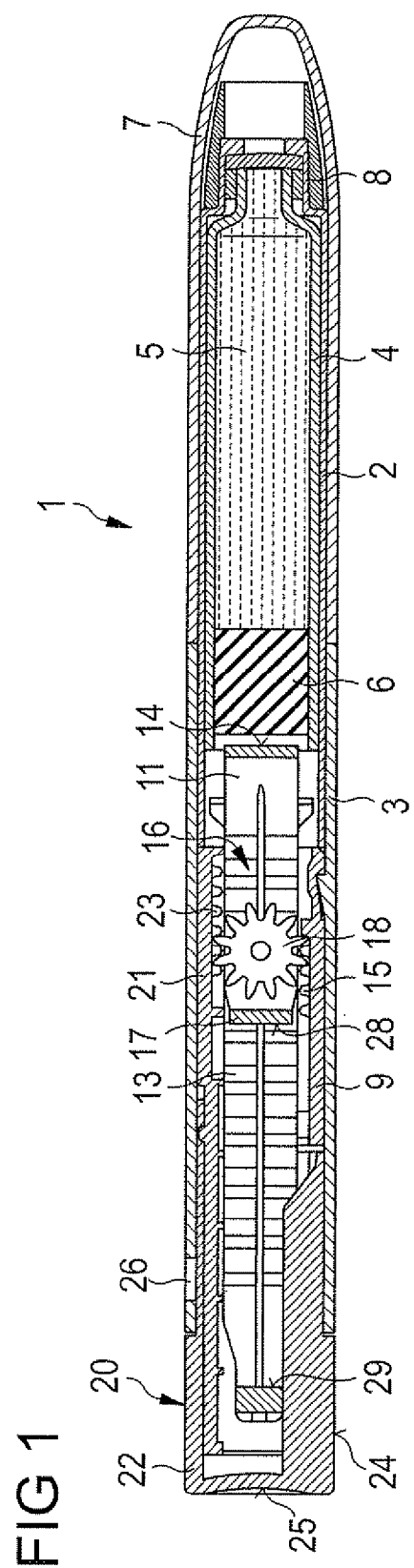
FIG. 1 shows a sectional view of a first embodiment of the medication delivery device in a first, cartridge full, position.

Referring to FIGS. 1 to 4, there is shown a medication delivery device in accordance with a first embodiment.

The medication delivery device 1 comprises a cartridge retaining part 2, and a main (exterior) housing part 3. The proximal end of the cartridge retaining part 2 and the distal end of the main housing part 3 are secured together by any suitable means known to the person skilled in the art. In the illustrated embodiment, the cartridge retaining part 2 is secured within the distal end of the main housing part 3.

A cartridge 4 is retained within the cartridge retaining part 2. A medication 5, for example a fluid medication as described above, is arranged within the cartridge 4. A piston 6 is retained within the cartridge 4. The piston 6 seals the medication within the cartridge 4 on the side of the proximal end of the cartridge. Distal movement of the piston 6 within the cartridge 4, in use, results in medication being dispensed from the cartridge.

A removable cap 7 is releasably retained over the distal end of the cartridge retaining part 2. The removable cap 7 may be provided optionally with one or more window apertures 30 through which the position of the piston 6 within the cartridge 4 may be viewed. The distal end of the cartridge retaining part 2 is provided with a distal threaded region 8 designed for the attachment of a suitable needle assembly to enable medication 5 to be dispensed from the cartridge 4.

The main housing part 3 is provided with an internal housing 9. The internal housing 9 is secured against rotational and axial movement with respect to the main housing part 3. Alternatively, the internal housing 9 may be formed integrally with the main housing part 3. The internal housing 9 is provided with a rack 15. The rack 15 extends along a main axis of the internal housing 9 and/or along a main axis of the external housing part 3. The main axis of the external housing part 3 may extend between the proximal end and the distal end of the main housing part.

Figure 1A:
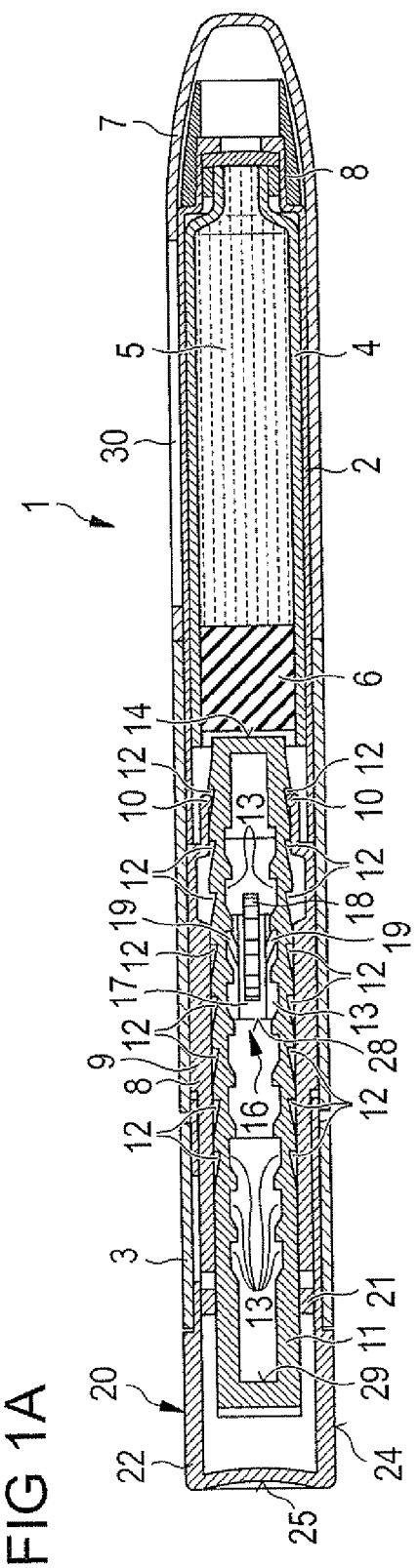
FIG. 1A shows a further sectional view of the first embodiment of the medication delivery device in the first, cartridge full, position.

Additionally, the internal housing 9 is provided with a plurality of guide lugs (not explicitly shown) and one or a plurality of restriction members 10 (see FIG. 1A), for example pawl means and/or ratchet means, like a ratchet pawl. The respective restriction member 10 may be an integrated part of the internal housing 9 or may be a separate component as it is illustrated in FIG. 1A for example. The respective restriction member 10 is fixed against rotational and axial movement with respect to the main housing part 3. The respective restriction member 10 may be a resilient restriction member. The respective restriction member may be arranged to be deformed radially.

The medication delivery device 1 comprises a piston rod 11. The piston rod 11 is arranged within main housing part 3. The piston rod extends along a main direction of extent of the main housing part 3. Restriction members 10 engage outer surfaces of the piston rod 11. These surfaces are arranged opposite with respect to one another.

The piston rod 11 is provided with a first set of indentations 12 on an external surface thereof. Preferably, two outer surfaces which are arranged opposite with respect to each other are provided with a corresponding first set of indentations 12. The indentations 12 are disposed along a main direction of extent of the piston rod 11. The respective restriction member 10 is arranged to engage an indentation 12 of the respective first set of indentation. The respective restriction member 10 is arranged to restrict proximal movement of the piston rod 11 with respect to the main housing part 3 during setting of a dose. This may be achieved by the restriction member 10 abutting a protrusion 27 forming the distal end of that indentation of the first set of indentations 12 which the restriction member 10 is arranged in, for example. The distal end of the respective indentation of the first set of indentations thus acts as a stop feature as described further above and below.

An inner surface of the piston rod 11 is provided with a second set of indentations 13. Two inner surfaces which are arranged opposite with respect to one another may be provided with a corresponding second set of indentations 13. The indentations 13 are disposed side by side along a main direction of extent of the piston rod 11.

The piston rod 11 is arranged to drive the piston 6 in the distal direction for delivering a dose of the medication 5. A bearing surface 14 located at the distal end of the piston rod 11 is disposed to abut the proximal face of the piston 6 and, in particular, to advance the piston 6 further into the cartridge 4 for delivering a dose of the medication 5. The bearing surface 14 as shown in FIGS. 1 and 1A, i.e. before the device is primed, is arranged at a distance from the piston 6, for example with an air gap formed between bearing surface 14 and piston 6. Alternatively, the bearing surface 14 may abut the proximal end face of the piston 6, thereby providing for a direct mechanical contact of piston rod 11 and piston 6, before the device 1 is primed.

The medication delivery device 1 has a gear 16, comprising a carrier 17 and a gear wheel 18. The gear wheel 18 and the carrier 17 are connected to one another. The gear wheel 18 is arranged to rotate within the carrier 17. The gear wheel may rotate with respect to the main housing part 3 and/or the internal housing 9. The gear 16 is located within a channel within the piston rod 11. Pawl arms 19 are provided on the carrier 17. The pawl arms 19 protrude from the carrier 17 in the radial direction. The pawl arms 19 are releasably engaged with a second set of indentations 13 of the piston rod 11. The pawl arms 19 of the carrier 17 are designed to transfer force to the piston rod 11 in the distal direction during dose delivery and to allow relative movement of the gear 16 with respect to the piston rod 11 in the proximal direction during dose setting. The teeth of the gear wheel 18 may be permanently engaged with the teeth of the rack 15 of the internal housing 9.

A drive member 20 extends about the piston rod 11. The drive member 20 comprises a rack part 21. The drive member 20 furthermore comprises an activation part 22. The rack part 21 and the activation part 22 are secured to each other to prevent rotational and axial movement therebetween. Alternatively, the drive member 20 may be a unitary component comprising integrated rack part 21 and integrated activation part 22. The drive member 20 is moveable in the proximal direction with respect to the main housing part 3 for setting a dose and in the distal direction with respect to the main housing part 3 for delivering the dose.

The rack part 21 is provided with a rack 23. The rack 23 may extend along the main axis of the rack part 21. The teeth of the rack 23 of the rack part 21 may be permanently engaged with the teeth of the gear wheel 18.

The drive member 20 has a plurality of guide slots (not explicitly shown) in which the guide lugs (not explicitly shown) of the internal housing 9 are located. These guide slots define the extent of permissible axial movement of the drive member 20 with respect to the main housing part 3. In the illustrated embodiment the guide slots may also prevent rotational movement of the drive member 20 relative to the main housing part 3.

The activation part 22 of the drive member 20 has a plurality of grip surfaces 24 and a dispensing face 25.

To increase intuitiveness of the operation of the device, the main housing part 3 may optionally be provided with a window aperture 26 through which graphical status indicators provided on the drive member 20, can be viewed.

FIG. 1B shows a simplified sectional view of a part of the medication delivery device described above, i.e. before the priming dose is dispensed (delivered) from the cartridge 4. The device is adapted to expel a small priming dose of medication during a first distal movement of the drive member 20 and the piston rod 11.

The bearing surface 14 of the piston rod 11, e.g. the distal end of the piston rod, is arranged at a distance $d_{PP}$ from the proximal end of the piston 6. Alternatively, the piston rod may abut the piston. The restriction members 10, for example resilient ratchet pawls, which are secured against rotational and axial movement with respect to the main housing part (not explicitly shown) engage the piston rod 11. The restriction member(s) 10 are biased radially inwards. The respective restriction member 10 is arranged within a first indentation 12a of the first set of indentations 12 that is provided on the outside of the piston rod 11. The respective restriction member 10 engages the piston rod 11. A distal end of the respective restriction member 10 is arranged at a first distance $d_F$ from the distal end (protrusion 27) of first indentation 12a. Piston rod 11 may be moved proximally during proximal movement of the drive member (not explicitly shown) for setting a dose by this first distance $d_F$ before the restriction member 10 abuts the stop feature (protrusion 27) and is prevented from further proximal movement.

The first indentation 12a may extend deeper into the piston rod 11 in the radial direction than one of or all of the further indentations 12b, 12c, 12c, 12d of the first set of indentations that are arranged further away from the distal end of the piston rod 11 than the first indentation 12a. As the medication delivery device may be stored in the condition shown in FIG. 1B, the respective restriction member is less stressed when it is arranged within the first indentation 12a than when it is arranged in another one of the indentations 12b, 12c, 12c, 12d. As mechanical stress on the restriction member 10 can be reduced in this way during storage of the device, the risk of material fatigue of the resilient restriction members 10 is reduced. The distal ends of the indentations 12a . . . 12d may be equidistantly disposed over the piston rod 11.

A drive element, like the pawl arms 19 of carrier 17, engages a first indentation 13a of the second set of indentations 13 provided on the inside of the piston rod. The drive element abuts the distal end of the first indentation 13a. The second set of indentations 13 comprises further indentations 13b, 13c, 13d, 13e which are arranged further away from the distal end of the piston rod 11 than the first indentation 13a. The distal end of the first indentation 13a and the distal end of the next indentation 13b are arranged closer to one another than distal ends of a different pair, preferably than distal ends of all different pairs of adjacent indentations of the second set of indentations 13.

Figure 2:
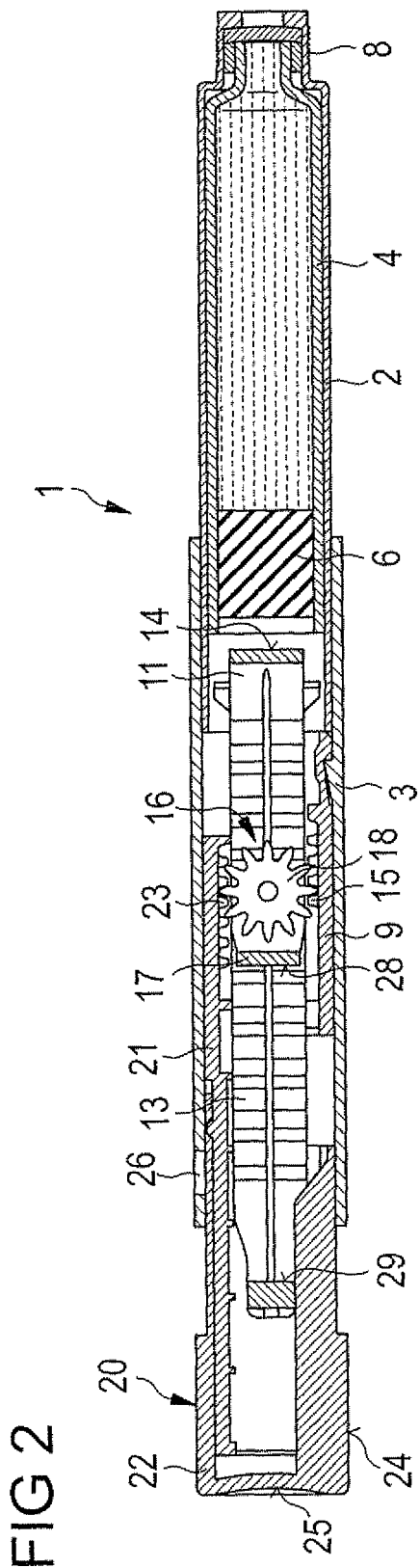
FIG. 2 shows a sectional view of the first embodiment of the medication delivery device in a second, priming dose set, position.

Operation of the medication delivery device in accordance with FIGS. 1 to 3 will now be described.

To set the priming dose the drive member 20 is moved proximally. For this purpose, a user grips the grip surfaces 24 of the drive member 20. The user then pulls the drive member 20 in a proximal direction away from the main housing part 3 thereby moving the rack part 21 in a proximal direction.

The proximal movement of the rack part 21 causes the gear wheel 18 to rotate and move proximally by virtue of the engagement of the teeth of the gear wheel 18 of the gear 16 with the teeth of the rack 23 of the rack part 21 and the teeth of the rack 15 of the internal housing 9 thus moving the gear 16 in the proximal direction with respect to the internal housing.

As the restriction members 10 allow for proximal movement of the piston rod 11 with respect to the internal housing 9 during the first proximal movement of the drive member 20 for setting the priming dose, the piston rod follows proximal movement of the drive member, preferably only during a part of the total proximal travel of the drive member 20. The proximal movement of the piston rod 11 may be achieved by friction between the radially outwardly biased pawl arms 19 of carrier 17 and piston rod within indentation 13a and/or mechanical contact of pawl arms 19 and the proximal end side of indentation 13a. Thus the piston rod 11 follows proximal movement of the gear 16 with respect to the internal housing 9.

The piston rod 11 is moved in the proximal direction until the restriction members 10 abut the protrusions 27 on the distal end of the respective first indentation 12a, i.e. piston rod 11 may be moved proximally by the distance $d_F$ during setting of the priming dose. After the restriction member 10 has abutted protrusion 27, the drive member 20 moves proximally with respect to the piston rod 11. After the respective restriction member 10 has moved into abutment with the protrusion 27, the piston rod is prevented from moving further proximally with respect to the internal housing 9. The gear 16 follows proximal movement of the drive member 20 with respect to internal housing 9 and piston rod 11. While the gear 16 moves proximally with respect to the piston rod 11, pawl arms 19 of carrier 17 move proximally from the first indentation 13a of the second set of indentations into the next indentation 13b in the proximal direction. The pawl arms 19 of the carrier 17 are pressed radially inwards by mechanical interaction of the pawl arms 19 with a ramp provided on the proximal end side of the first indentation 13a. The pawl arms 19 slide over the ramp and engage the next indentation 13b (cf. FIG. 2A). An audible and/or tactile feedback may be generated when the pawl arms 19 slide into the indentation 13b. Thereby, it may be indicated to the user that the priming dose was set. Additionally, visual feedback regarding setting of the priming dose may optionally be indicated by a graphical status indicator provided on the drive member 20, which can be viewed through the window aperture 26 in the main housing part 3.

This embodiment therefore has the advantage of allowing the piston rod 11 to move backwards by the distance $d_F$ during the first proximal movement of the drive member 20 ensuring that the length of the medication delivery device (e.g. pen injector) is minimised. At the same time it is also ensured that the audible click at the end of setting this first dose (e.g. priming dose) coincides with the end of the first dose setting stroke of the drive member 20 just as for any subsequent dose setting stroke (which preferably also coincides with the graphical status indicator).

The proximal travel of the drive member 20 is limited by the guide slots of the rack part 21. At the end of the travel of the drive member 20, the pawl arms 19 of the carrier 17 engage the next sequential indentation of the second set of indentations 13 of the piston rod 11 as indicated in FIGS. 2 and 2A. The pawl arms 19 rest in the first indentation 13a until the restriction member(s) 10 prevent further proximal movement of the piston rod 11 due to mechanical interaction of the respective restriction member with the stop feature (protrusion 27) of the piston rod 11. The piston rod 11 has been moved proximally by $d_F$ during setting of the priming dose. Thus, the distance between piston 6 and piston rod 11 is increased by $d_F$ after the priming dose has been set. The distance between piston rod and piston is $d_{PP}+d_F$ after the priming dose has been set.

When the priming dose has been set, the user may dispense this dose by depressing the dispensing face 25 of the activation part 22 of the drive member 20. By this action the drive member 20 and the rack part 21 are moved axially in the distal direction relative to the main housing part 3. As the teeth of the gear wheel 18 of the gear 16 are engaged with the teeth of the rack 23 of the rack part 21 and the teeth of the rack 15 of the internal housing 9, the gear wheel 18 of the gear 16 is caused to rotate and is moved in the distal direction. Thus, the gear 16 moves longitudinally in the distal direction with respect to the housing. As the pawl arms 19 of the carrier 17 of the gear 16 are engaged with the second set of indentations 12 of the piston rod 11, the piston rod 11 is caused to move longitudinally in the distal direction with respect to the internal housing 9. The gear 16, in particular the pawl arms 19, abuts a distal end side of the indentation 13b such that distal movement of the gear causes the piston rod 11 to be moved distally. The piston rod 11 moves only longitudinally. The piston rod 11 does not rotate with respect to the housing.

After the piston rod has been moved by $d_{PP}+d_F$ in the distal direction with respect to the housing, the bearing surface 14 of the piston rod 11 bears against the piston 6 of the cartridge 4 with continuing distal movement of the piston rod 11 causing the piston 6 to move distally, thereby causing the priming dose of medication to be dispensed, e.g. through an attached needle (not explicitly shown). Gaseous inclusions in cartridge and needle are removed in this way. Preferably, the medication delivery device is oriented with its distal end pointing upward (e.g. needle-up) for priming.

The distal travel of the drive member 20 may be limited by the guide slots (not explicitly shown) of the rack part 21.

When the piston rod 11 moves distally the restriction members 10 are pressed radially outwards and slide along a ramp before they engage the next indentation 12b of the first set of indentations. An audible and/or tactile feedback indicating that the priming dose has been dispensed may be caused by mechanical interaction of the restriction members 10 and the piston rod while the piston rod moves relative to the restriction members 10 and the restriction members are guided along the piston rod 11 into the next (second) indentation 12b (cf. FIG. 3). Additionally, visual feedback regarding dose dispensing may optionally be indicated by a graphical status indicator, provided on the drive member 20, which can be viewed through the window aperture 26 in the main housing part 3.

After the distal movement of the piston rod 11 for dose delivery the piston rod 11 may be moved proximally for a small distance in order to reduce pressure of the piston rod 11 on the piston 6 of the cartridge 4. Before the next dose is set, the distance between the distal end of the restriction member 10 and the distal end of the indentation 12b, 12c, 12d, . . . , which forms another stop feature, is expediently less than $d_F$. Preferably the restriction member 10 abuts the distal end of the second indentation already before the next dose is set. Proximal travel of the piston rod after priming is thus restricted by the restriction member which already interacts with the stop feature before the next dose is set.

The distal displacement of the piston rod 11 may be equal for all doses to be dispensed. In particular, the device 1 may be a fixed dose device, i.e. pre-set fixed doses are dispensed after the first distal movement of the piston rod 11, e.g. after the device has been primed. Due to the piston rod 11 being moved proximally (away from the piston 6) during the priming movement of the drive member 20, the priming dose is reduced accordingly, as the distal displacement of the piston within the cartridge is reduced by $d_F$. The distal displacement of the piston rod during dose delivery may be equal for the priming dose and one of or all of the subsequent doses to be dispensed.

The distal movement of the piston 6 with respect to the cartridge 4 for a second dose, preferably for all of the subsequent doses, which are to be dispensed, is preferably greater than the distal movement of the piston rod for dispensing the priming dose from the cartridge. Significant proximal movement of the piston rod 11, e.g. by $d_F$ or more, during proximal movement of the drive member for setting a dose after priming is expediently avoided.

Due to the piston rod being moved proximally before the priming dose is delivered, the length of the device may be reduced such as compared to a device where the piston rod is already arranged at a distance from the piston in an initial arrangement (e.g. when the unused pen is given to a patient) and no proximal movement of the piston rod away from the piston occurs before a given priming dose is expelled.

The audible and tactile feedback that the dose has been set or delivered may occur at corresponding points in time for the priming dose and subsequent doses to be dispensed.

Figure 4:
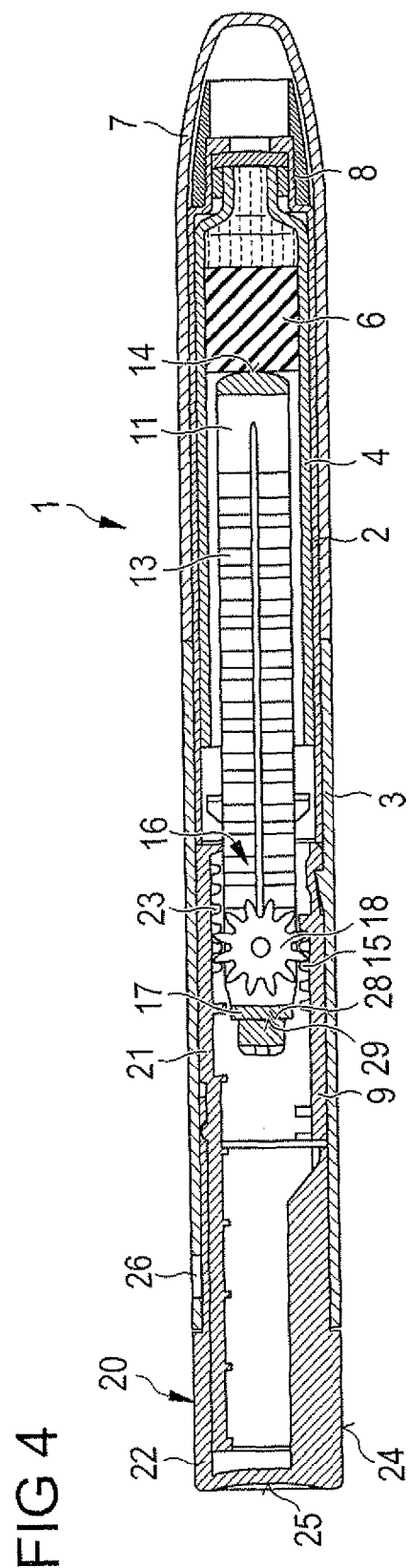
FIG. 4 shows a sectional view of the first embodiment of the medication delivery device in a forth, final dose delivered, position.

Further doses may be delivered as required up to a pre-determined maximum number of doses. FIG. 4 shows the medication delivery device in a condition where the maximum number of doses has been delivered. In this condition the proximal face 28 of the carrier 17 abuts an internal distal face 29 of the piston rod 11 to prevent further axial movement of the gear 16 and thus of the drive member 20 in the proximal direction. The device may be locked and made inoperable in this way after the maximum amount of doses has been dispensed.

A device similar to the one described in connection with FIGS. 1 to 4, in which the piston rod is moved only in the axial direction without rotation with respect to the housing, is described in WO 2008/058666 A1, the disclosure content of which is herewith explicitly incorporated by reference in the present application.

Referring to FIGS. 5 to 8, there is shown a medication delivery device in accordance with a second embodiment.

The medication delivery device 1 comprises a cartridge retaining part 2, and a main (exterior) housing part 3. The proximal end of the cartridge retaining part 2 and the distal end of the main housing 2 are secured together by any suitable means known to the person skilled in the art. In the illustrated embodiment, the cartridge retaining part 2 is secured within the distal end of the main housing part 3.

A cartridge 4 from which a number of doses of a medication 5 may be dispensed is provided in the cartridge retaining part 2. A piston 6 is retained in the proximal end of the cartridge 4.

A removable cap 7 is releasably retained over the distal end of the cartridge retaining part 2. The removable cap 7 is optionally provided with one or more window apertures 30 through which the position of the piston 6 within the cartridge 4 can be viewed.

In the illustrated embodiment the distal end of the cartridge retaining part 2 is provided with a distal threaded region 8 designed for the attachment of a suitable needle assembly (not shown) to enable medication 5 to be dispensed from the cartridge 4.

The main housing part 3 is provided with an internal housing 9. The internal housing 9 is secured against rotational and axial movement with respect to the main housing part 3. Alternatively, the internal housing 9 may be formed integrally with the main housing part 3. The internal housing 9 is provided with a threaded, preferably circular, opening 31. Opening 31 may comprise a protrusion 35. Protrusion 35 may be a thread or a part of a thread. Opening 31 may extend through the total internal housing 9. In the illustrated embodiment the threaded opening 31 comprises a series of part threads rather than a complete thread. Additionally, the internal housing 9 may be provided with a plurality of guide slots and pawl means (not explicitly shown).

A piston rod 11 is arranged within main housing 3. A first thread 32 is formed at the distal end of the piston rod 11. The piston rod 11 may be of generally circular cross-section. The first thread 32 of the piston rod 11 extends through and is threadedly engaged with the threaded opening 31 of the internal housing 9. The first thread 32 is formed on the outside of the piston rod 11. A pressure foot 33 is located at the distal end of the piston rod 11. The pressure foot 33 is disposed to abut the proximal face of the piston 6. The piston rod 11 is arranged at a distance $d_{PP}$ from the piston 6. Preferably, distance $d_{PP}=0$ and the pressure foot 33 abuts the piston 6.

A second thread 34 is formed at the proximal end of the piston rod 11. The second thread 34 is formed on the outside of the piston rod 11. In the illustrated embodiment the second thread 34 comprises a series of part threads, rather than a complete thread. The second thread 34 is formed on flexible arms 36 of the piston rod 11.

The first thread 32 and the second thread 34 are oppositely disposed.

A drive member 20, for example a drive sleeve, extends about the piston rod 11. The drive member 20 comprises a threaded part 37. The threaded part 37 may be arranged on the inside of the drive member 20. The threaded part 37 may be of a generally cylindrical cross-section. The drive member 20 additionally comprises an activation part 22. The threaded part 37 and the activation part 22 are secured to each other to prevent rotational and/or axial movement therebetween. Alternatively, the drive member 20 may be a unitary component consisting of an integrated threaded part 37 and activation part 22.

In the illustrated embodiment the threaded part 37 is provided with a longitudinally extending (helical) thread 38 formed on an internal surface of the drive member 20.

The flank of the distal side of the thread 38 is designed to maintain contact with the second thread 34 of the piston rod 11 when dispensing a dose. The flank of the proximal side of the thread 38 is designed to allow the second thread 34 of the piston rod 11 to disengage from the thread 38 during setting of a dose. In this way the thread 38 of the threaded part 37 is releasably engaged with the second thread 34 of the piston rod 1. Consequently, the drive member 20 and the piston rod are releasably engaged.

The drive member 20 has a plurality of features formed on the external surface designed to move axially within the guide slots of the internal housing 9 (not explicitly shown). These guide slots define the extent of permissible axial movement of the drive member 20 with respect to the main housing part 3. The guide slots may also prevent rotational movement of the drive member 20 relative to the main housing part 3.

The activation part 22 of the drive member 20 has a plurality of grip surfaces 24 and a dispensing face 25.

To increase intuitiveness of the operation of the device, the main housing part 3 may be provided with a window aperture through which graphical status indicators, provided on the drive member 20, can be viewed.

Figure 5A:
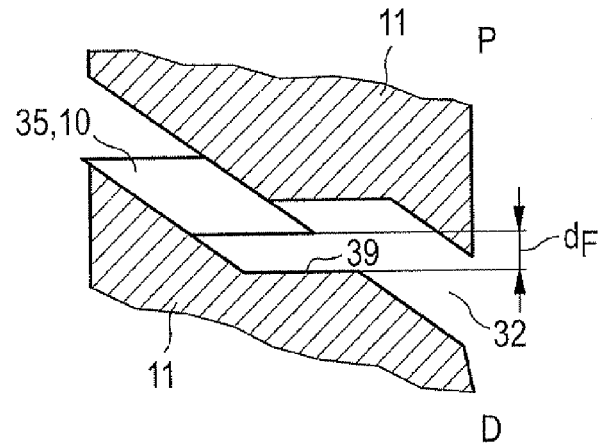
FIG. 5A shows an enlarged simplified view of a part of the second embodiment of the medication delivery device in the first, cartridge full, position.
Figure 5B:
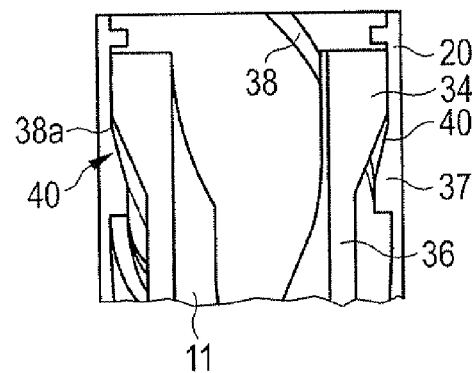
FIG. 5B shows an enlarged simplified view of another part of the second embodiment of the medication delivery device in the first, cartridge full, position.
Figure 6:
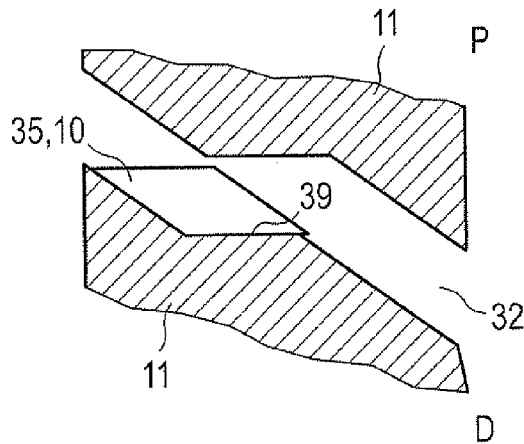
FIG. 6 shows an enlarged simplified view of the part of the second embodiment of the medication delivery device shown in FIG. 5A during setting of the priming dose.
Figure 7A:
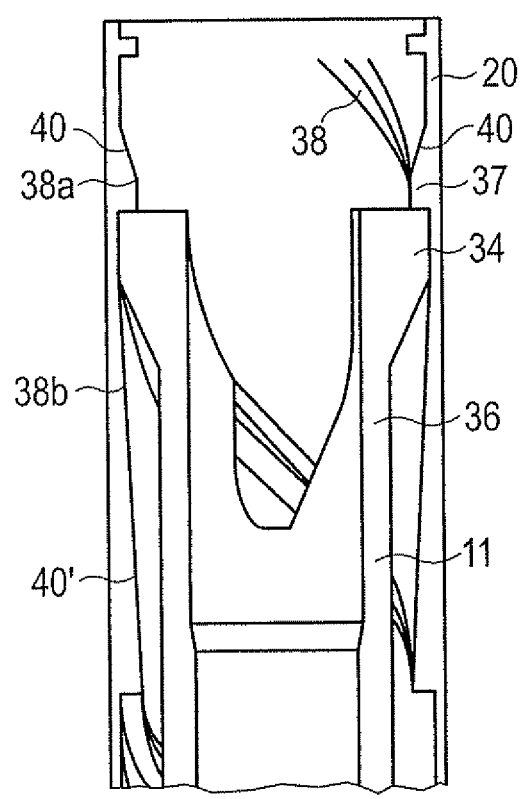
FIG. 7A shows an enlarged simplified view of a part of the second embodiment of the medication delivery device in the second, priming dose set, position.

As in the previous embodiment, the piston rod 11 is arranged at a distance $d_{PP}$ from the piston 6 before the priming dose is set (cf. FIG. 5). Alternatively, the pressure foot 33 may abut the piston 6 before the priming dose is set.

The first thread 32 of the piston rod 11 is provided with a plurality of stop features. The stop features are arranged to mechanically interact with a restriction member 10 in order to restrict or prevent proximal movement of the piston rod with respect to the housing 3. The respective stop feature may be a flattened step 39 of the first thread 32 (cf. FIG. 5A). The respective stop feature may be embodied as a region that has a thread angle differing from the thread angle in adjacent regions of first thread 32, for example. Of course, a shoulder or a dip in the first thread 32 is also suitable as a stop feature. The protrusion 35 within opening 31 may serve as restriction member 10.

FIG. 5A shows a partial view of the piston rod 11 in that region in which first thread 32 and restriction member 10 are engaged with one another. That side of FIG. 5A that is closest to the distal end is labelled D and that side which is closest to the proximal end is labelled P. FIG. 5A only shows one step. However, the first thread 32 preferably comprises a plurality of steps 39 that are disposed at equal distances as seen along the thread. After delivery of a dose, i.e. after the piston rod 11 has advanced the piston 6 further into the cartridge 4, the restriction member 10 is arranged to mechanically interact or already interacts with a different stop feature (not shown) than the stop feature the restriction member was arranged to mechanically interact with before that particular dose was delivered.

The restriction member 10 may have a parallelogram-like or trapezoid-like cross section. The restriction member 10 is arranged at a distance $d_F$ from the stop feature before the priming dose is set (cf. FIG. 5A). This allows for a proximal movement of the piston rod 11 with respect to the restriction member 10 before the priming dose is delivered as described in connection with the previous embodiment. In contrast to the previous embodiment, the piston rod 11 is adapted to be rotated and translated with respect to the housing while the piston rod is moved distally for dose delivery. Of course, the piston rod is also rotated and translated when it is moved proximally during the first proximal movement of the drive member.

Operation of the medication delivery device in accordance with the present embodiment will now be described.

To set the priming dose a user grips the grip surfaces 24 of the drive member 20. The user then pulls the drive member 20 in a proximal direction away from the main housing part 3. The drive member 20 does not rotate during this proximal movement.

The piston rod 11 follows part of the proximal movement of the drive member 20 with respect to the housing due to the piston rod interacting with the drive member 20 and due to the restriction member 10 not preventing this first proximal movement. A turn 38a of the thread 38 may comprise a ramp 40 that rises as it extends in the distal direction. Ramp 40 may extend distally only over a part of turn 38a. The second thread 34 of the piston rod 11 is arranged on the proximal side of ramp 40 before the (priming) dose is set. Due to friction between piston rod and drive member 20, in particular between the second thread 34 of the piston rod and ramp 40, the piston rod 11 follows the first movement of the drive member 20 in the proximal direction.

The piston rod 11 follows the proximal movement of the drive member 20 with respect to the housing until the restriction member 10 mechanically interacts with the stop feature, i.e. step 39, of the first thread 32, e.g. by mechanical contact. The piston rod rotates with respect to the housing and the drive member during proximal movement of the piston rod with respect to the housing. Piston rod 11 is moved proximally by the distance $d_F$ until further proximal movement of the piston rod 11 with respect to the housing 3 is restricted by the stop feature interacting mechanically with the restriction member 10 (cf. FIGS. 5A and 6).

As proximal movement of the drive member 20 continues, the stop feature 39 and the restriction member 10 stay in mechanical interaction and the drive member is moved proximally with respect to the piston rod 11. Interaction of the stop feature and the restriction member 10 prevents further proximal movement of the piston rod 11 with respect to the housing 3 and the piston 6. Thus, the initial distance $d_{PP}$ between piston rod 11 and piston 6 is increased by $d_F$ to $d_{PP}+d_F$.

While the drive member 20 is moved proximally with respect to the piston rod 11, the flexible arms 36 of the piston rod are displaced radially inwardly and move over the distal end of ramp 40. Thereby, the next turn 38b of thread 38 of the drive member 20 may be engaged by the thread 34 of the piston rod under the action of the flexible arms 36. An audible and tactile feedback that the priming dose was set may be generated when the proximal end of the piston rod slides over the distal end of the ramp 40.

Additionally, visual feedback regarding dose setting may be indicated by an optional graphical status indicator, provided on the drive member 20, which can be viewed through an optional window aperture in the main housing part 3.

The ramp 40' in the next turn 38b of thread 38 may have a smaller slope than the ramp 40 in the turn 38a. Ramp 40' may extend distally over the total turn 38b. Play between drive member 20 and piston rod 11 may thus be reduced after the device 1 has been primed.

When the priming dose has been set, the user may then dispense this dose by depressing the dispensing face 25 of the activation part 22 of the drive member 20. By this action the drive member 20 is moved axially in the distal direction relative to the main housing part 3. As the second thread 34 of the piston rod 11 is positively engaged with the thread 38 of the drive member 20, the piston rod 11 is caused to rotate with respect to the internal housing 9 by the axial movement of the drive member 20 in the distal direction. As the piston rod 11 rotates, the first thread 32 of the piston rod 11 rotates within the opening 31 of the internal housing 9, thereby causing the piston rod 11 to move axially in the distal direction with respect to the internal housing 9.

After the piston rod 11 has traveled by $d_{PP}+d_F$ the pressure foot 33 of the piston rod 11 bears against the piston 6. Further distal movement of the piston rod 11 causes the piston to move distally with respect to the cartridge 4 and a dose of medication to be expelled from the cartridge 4.

The distal travel of the drive member 20 is limited by the guide slots (not explicitly shown) of the internal housing 9. Audible and tactile feedback to indicate that the priming dose has been dispensed is provided by the interaction of the detent (not explicitly shown) of the drive member with the pawl means (not explicitly shown) of the internal housing 9. Additionally, visual feedback regarding dose dispense may be indicated by an optional graphical status indicator provided on the drive member 20, which can be viewed through an optional window aperture in the main housing part 9.

Further doses may be delivered as required up to a pre-determined maximum number of doses.

In the illustrated embodiment the first thread 32 is expediently provided with a plurality of stop features 39 that may cooperate with restriction member 10 in opening 31 to restrict movement of the piston rod 11 in the proximal direction during setting of the second and any subsequent dose to be delivered. The restriction member may interact with a different one of the stop features before and during setting of a subsequent dose. Thus, as the piston rod is not moved significantly in the proximal direction during setting of a second and preferably any dose subsequent to the priming dose, the (fixed) doses which may be dispensed after priming may be greater than the priming dose given a fixed distal displacement of the piston rod during delivery of each dose.

Further doses may be delivered from the cartridge until a maximum number of doses has been delivered. FIG. 8 shows the medication delivery device 1 in a condition where the maximum number of doses has been delivered. In this condition, lug features 41 on the piston rod 11 may interlock with lug features 42 on the drive member 20 to prevent further axial movement of the drive member 20 in the proximal direction with respect to the housing.

The audible and tactile feedbacks that the dose has been set or delivered may occur at corresponding points in time for the priming dose and subsequent doses to be dispensed.

A device similar to the one described in connection with FIGS. 5 to 8, in which the piston rod is moved in the axial direction and rotates with respect to the housing, is described in WO 2008/058665 A1, the disclosure content of which is herewith explicitly incorporated by reference in the present application.

The invention claimed is:

1. A drive assembly for use in a medication delivery device, comprising:
   a housing having a proximal end and a distal end,
   a drive member moveable in a proximal direction with respect to the housing for setting a dose of the medication to be delivered and in a distal direction with respect to the housing for delivering the dose,
   a piston rod adapted to be driven by the drive member in the distal direction with respect to the housing during movement of the drive member in the distal direction for delivering the dose, wherein the piston rod includes at least one indentation disposed along an exterior peripheral surface of the piston rod and configured as a stop feature, and
   a restriction member protruding radially inward from the housing and configured to interact mechanically with the stop feature of the piston rod for restricting a proximal movement of the piston rod with respect to the housing during a proximal movement of the drive member,
   wherein
   the restriction member and the stop feature are arranged for the piston rod to be moved proximally a first distance during a first proximal movement of the drive member before the restriction member and the stop feature interact mechanically, wherein the first distance which the piston rod moves proximally during the first proximal movement of the drive member is larger than a subsequent distance which the piston rod moves proximally during a subsequent proximal movement of the drive member, and
   wherein the piston rod comprises a plurality of stop features, the drive assembly being configured for the restriction member to mechanically interact with a different stop feature after distal movement of the drive member for dose delivery.

2. The drive assembly according to claim 1, wherein a priming movement of the drive member comprises the first proximal movement of the drive member.

3. The drive assembly according to claim 1, wherein the drive member and the piston rod are releasably engaged.

4. The drive assembly according to claim 1, wherein the restriction member engages the piston rod.

5. The drive assembly according to claim 1, wherein the restriction member is secured against at least one of or both of rotational movement with respect to the housing and axial movement with respect to the housing.

6. The drive assembly according to claim 1, wherein the stop feature is provided on an outer surface of the piston rod.

7. The drive assembly according to claim 1, wherein the plurality of stop features are arranged equidistantly along the piston rod.

8. The drive assembly according to claim 1, wherein the piston rod and the restriction member are arranged for the proximal movement of the piston rod to be prevented during a second and any subsequent proximal movement of the drive member for setting the dose by the restriction member already mechanically interacting with one of the plurality of stop features before the second and any subsequent proximal movement of the drive member for setting the dose.

9. The drive assembly according to claim 1, wherein the drive assembly is configured for rotational movement of the piston rod with respect to the housing to be restricted.

10. The drive assembly according to claim 1, wherein the drive assembly is configured for the piston rod to be rotatable with respect to the housing.

11. The drive assembly according to claim 1, wherein the piston rod comprises a thread and the restriction member engages the thread of the piston rod.

12. The drive assembly according to claim 11, wherein the restriction member is a thread or a part of a thread.

13. The drive assembly according to claim 11, wherein the thread of the piston rod comprises the stop feature with the stop feature being a region of the thread that has a different thread angle as compared to an adjacent region of the thread.

14. The drive assembly according to claim 1, wherein the first distance is greater than a distance which the piston rod moves proximally subsequent to a distal movement of the piston rod for delivering the dose.

* * * * *

UNITED STATES PATENT AND TRADEMARK OFFICE
CERTIFICATE OF CORRECTION

PATENT NO. : 9,731,079 B2
APPLICATION NO. : 13/131521
DATED : August 15, 2017
INVENTOR(S) : David Plumptre Page 1 of 1

It is certified that error appears in the above-identified patent and that said Letters Patent is hereby corrected as shown below:

On the Title Page

At item (60) (Related U.S. Application Data), please insert -- U.S. Application No. 12/326,131, filed on Dec. 2, 2008 --

At item (30) (Foreign Application Priority Data), please insert -- Dec. 2, 2008 (EP) ........ 08020872.1 --

Signed and Sealed this
Third Day of October, 2017

Joseph Matal
*Performing the Functions and Duties of the*
*Under Secretary of Commerce for Intellectual Property and*
*Director of the United States Patent and Trademark Office*